United States Patent [19]

Burzio

[11] Patent Number: 5,410,023
[45] Date of Patent: Apr. 25, 1995

[54] PEPTIDE USEFUL AS ADHESIVE, AND PROCESS FOR THE PREPARATION THEREOF

[76] Inventor: Luis O. Burzio, Arica 2233, Valdivia, Chile

[21] Appl. No.: 993,893

[22] Filed: Dec. 18, 1992

Related U.S. Application Data

[63] Continuation of Ser. No. 371,734, Jun. 27, 1989, abandoned.

[51] Int. Cl.$^6$ .......................... A61K 37/02; C07K 1/06
[52] U.S. Cl. ..................................................... 530/329
[58] Field of Search ....................... 530/327, 328, 329; 514/16

[56] References Cited

U.S. PATENT DOCUMENTS

| | | | |
|---|---|---|---|
| 4,496,397 | 1/1985 | Waite | 106/161 |
| 4,585,585 | 4/1986 | Waite | 260/112.5 R |
| 4,687,740 | 8/1987 | Waite | 435/68.1 |
| 4,808,702 | 2/1989 | Waite | 530/328 |

OTHER PUBLICATIONS

Waite, "Marine Adhesive Proteins: Models for a New Generation of Polymers?".
Dr. J. H. Waite, "Marine Adhesive Proteins: Models for a New Generation of Polymers?", (undated manuscript made available at the 2nd International Symposium of New Materials held in Osaka, Japan, Oct. 1988).
Filpula et al.; "Structural and Functional Repetition in a Marine Mussel Adhesive Protein", Biotechnology Progress in Press May/Jun. Issue 1989.
Strausberg et al., "Development of a Microbial System for Production of Mussel Adhesive Protein"; ACS Symposium Series 385 (1989).
Waite, et al., Sci. 212, 1981, pp. 1038-1040.
Waite, et al. Biochemical And Biophysical Research Communications, vol. 96 (4), 1980, pp. 1554-1561.
Bendedict, et al., Aug. 30-Sep. 4, 1987.
Young, et al., Chapter 2.
Waite, J. H. (1989) New Ceramics Preprint.
Burzio, et al., Abstract p. 4-13.
Burzio, L. O. Abstract.
Waite, J. H. Biol. Rev. 58: 209-231.
Waite, J. H. (1985) Biochemistry 24: 5010-6014.
Waite, J. H. (1983) J. Biol. Chemistry 258: 2911-2915.
Waite, J. H. (1986) J. Comp. Physiol. B 156: 491-496.

Primary Examiner—Jill A. Warden
Assistant Examiner—S. G. Marshall
Attorney, Agent, or Firm—Jacobson, Price, Holman & Stern

[57] ABSTRACT

A peptide of the formula:

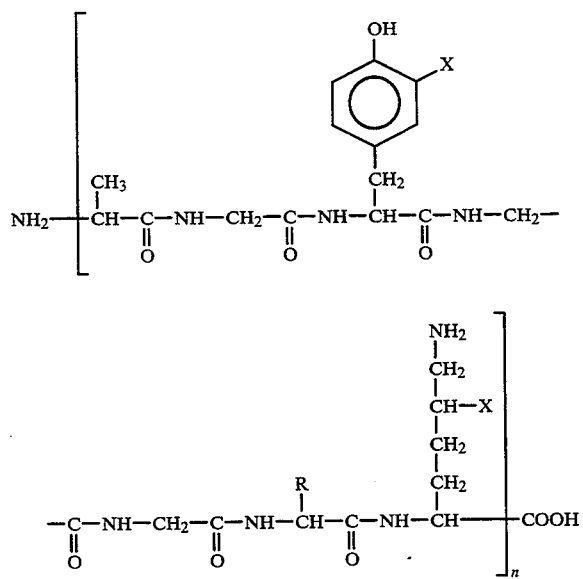

wherein each substituent X is independently a hydrogen atom or a hydroxyl group, each substituent R is a methylethyl, 1-methylpropyl, or 2-methylpropyl group, so that the penultimate group from the C-terminal of each of the n units is a valine, isoleucine, or leucine, and n is an integer of from 1 to about 1000, can be produced from mussels. This peptide is useful as an adhesive.

2 Claims, No Drawings

PEPTIDE USEFUL AS ADHESIVE, AND PROCESS FOR THE PREPARATION THEREOF

This application is a continuation of application Ser. No. 07/371,734, filed Jun. 27, 1989, now abandoned.

FIELD OF THE INVENTION

This invention relates to a peptide useful as an adhesive and to a process for the preparation thereof.

BACKGROUND OF THE INVENTION

It is known that peptides useful as adhesives can be obtained from mussels of the genus Mytilus, and more specifically from the phenol gland of such mussels. A decapeptide of this type is described in U.S. Pat. No. 4,585,585 issued Apr. 29, 1986 to Waite. Waite and his co-workers have further described this decapeptide and its use as an adhesive in Biochem. Biophys. Res. Commun., 96:1554–1561 (1980); Science, 212:1038–1040 (1981); J. Biol. Chem., 258:2911–2915 (1983); Biochemistry, 24:5010–5014 (1985); J. Comp. Physiol B, 156:491–496 (1986); Int. J. Adhesion and Adhesives, 7:9–14 (1987). The adhesive described in these publications exhibits unusually effective adhesive properties on many surfaces, including surfaces submerged in water. However, the process described by Waite for the purification of bioadhesive protein involves disection of the gland from the mussel foot, differential extraction procedures and several chromatographic steps to yield a polyphenolic protein of high purity.

It has now been discovered that phenol gland of certain mussels of the genus Mytilus can also be made to yield an adhesive polyphenolic protein which is different from that described by Waite and which is based upon a heptapeptide repeating unit. Furthermore, it has been discovered that the extraction of this new adhesive peptide from mussels can be accomplished by a process which is simpler and less expensive than that described by Waite, thereby reducing the difficulties in scaling-up the process to a commercial level.

SUMMARY OF THE INVENTION

Accordingly, the invention provides a substantially pure polyphenolic protein of the formula:

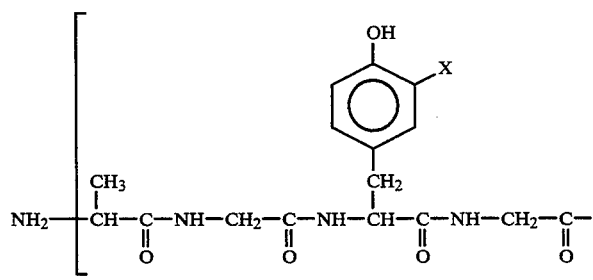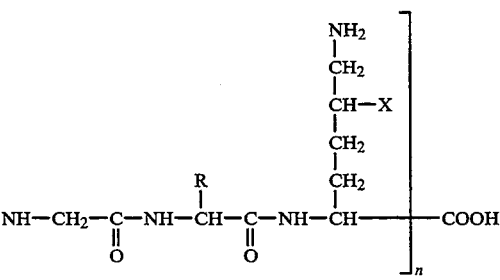

wherein each substituent X is independently a hydrogen atom or a hydroxyl group, each substituent R is a methylethyl, 1-methylpropyl or 2-methylpropyl group, so that the penultimate group from the C-terminal of each of the n units is a valine, isoleucine or leucine, and n is an integer of from 1 to about 1000.

This invention also provides a polyphenolic protein which comprises from 2 to about 1000 repeating units of the above formula wherein each substituent X is independently a hydrogen atom or a hydroxyl group, and the substituent R is a methylethyl, 1-methylpropyl or 2-methylpropyl group, so that the penultimate group from the C-terminal of each of the repeating units is a valine, isoleucine or leucine, adjacent pairs of the repeating units being connected to one another via peptide linkages, oligopeptides or bifunctional coupling agents. The amino acid sequence of the heptapeptide sequence is:

"-ALA-GLY-(TYR or DOPA)-GLY-GLY-(VAL or LEU or ILE)-(LYS or HO-LYS)-".

Finally, this invention provides a process for the preparation of an adhesive polyphenolic protein, which process comprises:

(a) homogenizing tissue from the mussel foot selected from the group consisting of Aulacomya ater, Choromytilus chorus, Mytilus chilensis, and Perumytilus purpuratus, the homogenizing being performed under an inert atmosphere;

(b) separating the solid phase from the resultant homogenate;

(c) rehomogenizing the solid phase in an acidic solution and separating the supernatant liquid from the resultant homogenate;

(d) dialyzing the supernatant liquid against an aqueous solution of sodium borate; and (e) precipitating the adhesive protein from the non-dialyzable fraction produced in step (d) by adding at least one volume of acetone or three volumes of ethanol to this fraction. Methanol or other solvents can be used.

The homogenizing step (a) does not require previous disection of the phenol gland.

DETAILED DESCRIPTION OF THE INVENTION

The adhesive polyphenolic protein of the invention can be depolymerized to heptapeptide form by treatment with trypsin in a neutral or weakly basic buffer. The heptapeptide thus produced can be purified by reverse-phase high pressure liquid chromatography on a C-8 column, and can then be linked to form adhesive polymers either by treatment with a bifunctional reagent such as glutaraldehyde, or by coupling via linking groups such as amino acids, oligopeptides, or other bifunctional spacers. The bioadhesive polyphenolic proteins, comprising at least 200 heptapeptide units, give very viscous solutions, but exhibit the best adhesive properties. In general, it is recommended that the adhesive polymers be stored in solutions not exceeding about 10 milligrams per milliliter of polymer, since more concentrated solutions show a tendency to gelatinize. Also, it is desirable to store the solutions under an inert gas such as nitrogen or under vacuum.

The polyphenolic protein solutions are stable and nonadhesive so long as they are maintained in acid solution at around pH 3. This pH is conveniently maintained with an acetic acid buffer. To use the protein solution as an adhesive, it is only necessary to raise its pH to about neutral, conveniently by addition of an alkaline buffer to the acid solution, and contact the neutralized solution with the surfaces to be adhered to one another.

The adhesive polymers of this invention may be employed in, for example:

a) Adhering cells to petri dishes or other solid supports can be achieved.

b) Several adhesive uses in medicine and dentistry can be provided. Medical uses can include the repair of lacerated or otherwise damaged organs, especially broken bones and detached retinas and corneas. Also the adhesive can be used to block the fallopian tubes of women as a sterilization procedure. Dental uses include the repair of dental caries, as a permanent sealant, and an adhesive for periodontal surgery.

c) The adhesive can adhere antigens or antibodies to a support, for example, in ELISA assays. In this use, the normally plastic support wall is coated with the adhesive and then the antigens or the antibodies are placed on the adhesive and hence adhered to the support.

d) Industrial uses can also be achieved. These including the coating of microelectronic components. The adhesive acts as a corrosion preventer and a conductive adherent since the bioadhesive conducts electricity. In the ship industry, the adhesive can be used to coat the hull to prevent fouling by marine growth and corrosion.

e) The adhesive can immobilize enzymes and bacteria to glass beads or other plastic supports for the construction of industrial bioreactors.

The preferred peptides of the present invention are those in which each substituent X is a hydroxyl group and in which each substituent R is a methylethyl group, so that the penultimate residue from the C-terminal of each unit is a valine residue.

The preferred mussel for extraction of the adhesive protein of the present invention is *Aulacomya ater*, since this mussel has been found to produce the polyphenolic protein from which the heptapeptide described in this invention was isolated. Furthermore, this mussel gives a high yield of the adhesive protein. While the process described by Waite (see above) typically yields about 2 to 3 mg of his adhesive protein per 100 phenol glands or mussel feet from, for example, *Mytilus edulis*, the process of the present invention normally yields about 5 times as much of the instant adhesive protein of *Aulacomya ater*, as thus about 15 mg of adhesive protein per 100 mussel feet.

In the process of the present invention, the presence of even trace amounts of heavy metals (such as are often found in many of the reagents which must be employed) can cause premature setting of the adhesive polyphenolic protein. To overcome this problem, it is desirable to add a chelating agent, such as ethylenediamine tetraacetic acid to the homogenate in step (a) and to the dialysis medium against sodium borate in step (d). However, this chelating agent should be removed by dialysis prior to the precipitation in step (e), so that it does not interfere with such precipitation. Also, because of the sensitivity of the adhesive polyphenolic protein to atmospheric oxygen, it is desirable to include an oxygen scavenger in the solution used for rehomogenizing in step (c). A recommended scavenger for this purpose is 2-mercaptoethanol. It is desirable to include a trypsin inhibitor in the solution used for the first homogenization to avoid degradation of the adhesive peptide by any trypsin-like activity naturally present in the mussels. Finally, it has been found advantageous to include a surface active agent in the aqueous solution used for the dialysis against sodium borate. Suitable surface active agents are sold commercially. One such agent is sold under the mark "TRITON X-100".

The method of this invention can include three dialysis steps. The first dialysis step is against cold water to lower the concentration of acetic acid before the second dialysis step against 0.1M sodium borate (plus other components). This second dialysis step is important because it precipitates the contaminating collagen leaving the polyphenolic protein in solution. The third dialysis step against acetic acid is to eliminate most of the sodium borate and the EDTA, and also to lower the pH of the solution containing the polyphenolic protein.

Although the heptapeptides of the present invention have hitherto been produced from the polyphenolic protein extracted from the specified mussels, such heptapeptides can of course also be synthesized from their constituent amino acids using techniques which are familiar to those skilled in the art of peptide synthesis. For example, solid state synthesis of the monomeric heptapeptide followed, if desired, by polymerization of this heptapeptide by any of the polymerization techniques already described.

The following Example is now given, though by way of illustration only, to show details of reagents, conditions, and techniques used in a preferred embodiment of the process of the present invention.

EXAMPLE

Mussels of the species *Aulecomya ater* were obtained from fishing off the Chilean coast and the foot of each mussel was amputated at its base and transferred to liquid nitrogen. Between 250 to 1000 grams of feet were prepared in this manner. The present procedure does not require the previous disection of the phenol gland from the foot of the mussel which is time consuming and difficult to perform. Accordingly, 10 g. of frozen feet were homogenized at 4° C. in a Waring blender under a nitrogen atmosphere in 100 ml. of a 50 mM Tris-HCl buffer (pH 7.5) 1M in NaCl, 25 mM in ethylenediamine tetraacetic acid (EDTA), 5 mM ethylene glycol-bis ($\beta$-aminoethyl ether)N,N,N',N'-tetraacetic acid (EGTA), 1 mM in phenylmethylsulfonyl fluoride, 1 mM in potassium cyanide, and 10 mM in N-ethylmaleimide, and containing 20 $\mu$g per milliliter of soybean trypsin inhibitor. The resulting homogenate was centrifuged at 3000 g for 10 minutes and the supernatant liquor discarded. The centrifugate was re-homogenized under the same conditions as before, but in 100 ml. of 0.9M acetic acid, 10 mM in 2-mercaptoethanol, and 1 mM in phenylmethylsulfonyl fluoride. The resulting homogenate was centrifuged at 10,000 g for 30 minutes at 4° C., the centrifugate discarded, and only the supernatant liquor, which contained the polyphenolic protein retained.

This supernatant liquor was dialyzed against 100 volumes of cold distilled water for 4 hours, and against 100 volumes of 0.1M sodium borate solution (pH 8.7) containing 0.1% of "TRITON X-100" surface active agent and 5 mM in ethylenediamine tetraacetic acid. The nondialyzable fraction was centrifuged at 5,000 g for 15 minutes and the clear supernatant liquor obtained was again dialyzed against 0.9M acetic acid for 4 hours at 4° C.

The non-dialyzable fraction thus obtained was then mixed with one volume of acetone or, alternatively, three volumes of ethanol, and additions were made thereto to produce a solution containing 0.01% "TRITON X-100", 0.15M in HCl, and 25 mM in 2-mercaptoethanol. The resultant solution was allowed to stand overnight at −20° C. and the polyphenolic protein which has precipitated therefrom separated by centrifugation at 5,000 g for 10 minutes at 4° C. The centrifugate was dissolved in a small amount of 0.9M acetic acid, separated into aliquots and stored under nitrogen in closed plastic tubes.

For further purification of the adhesive polyphenolic protein, the above concentrated fraction was subjected to gel permeation chromatography using a column for high pressure liquid chromatography. The chromatography was performed on a polystyrene polyhdroxylated column (Shimadzu; Shim-Pack, SHG-30W, 7.9 mm×250 mm) at a flow rate of 1 ml per minute using a solvent mixture containing 30% acetonitrile, 5% acetic acid, 1 mM ethylenediamine tetraacetic acid, and 0.02% cetyltrimethyl ammonium bromide. The fraction containing dihydroxyphenylalanine (DOPA) was pooled, precipitated with acetone or, alternatively, ethanol as described before, dissolved in 0.9N acetic acid, and stored under nitrogen in closed tubes. If required, final purification was achieved by reverse-phase chromatography on a C-8 column (Lichrosorb from Merck; 250 mm×4.5 mm) using a shallow linear gradient of acetonitrile in 0.1% trifluoroacetic acid according to the procedure described by Waite, et al. (*Biochemistry*, 24:5010-5014, 1985).

To determine the structure of the polyphenolic protein thus obtained, a sample of the protein was digested with trypsin in the manner described in Example 2 of Waite's aforementioned U.S. Pat. No. 4,585,585, herein incorporated by reference. This digestion produced a mixture of six heptapeptides having the common amino acid composition of GLY, ALA, DOPA or TYR, and LYS or HYL. In addition, the amino acids VAL, ILE, and LEU were found in the product. These peptides were resolved and purified by reverse phase high pressure liquid chromatography on a C-8 column, and analyzed in a sequencer. The results of this analysis showed that the heptapeptide mixture isolated from the polyphenolic protein isolated from *Aulacomya ater* had the following common structure:

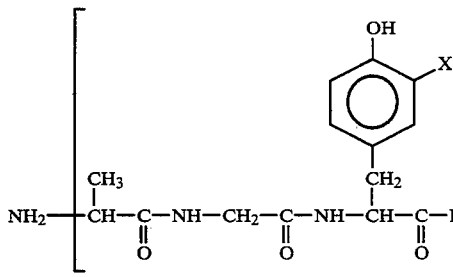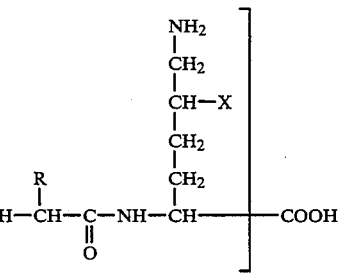

wherein each substituent X is independently a hydrogen atom or a hydroxyl group, each substituent R is a methylethyl, 1-methylpropyl, or 2-methylpropyl group, so that the penultimate group from the C-terminal of said peptide is a valine, isoleucine or leucine.

What is claimed is:

1. A biologically pure heptapeptide of the formula:

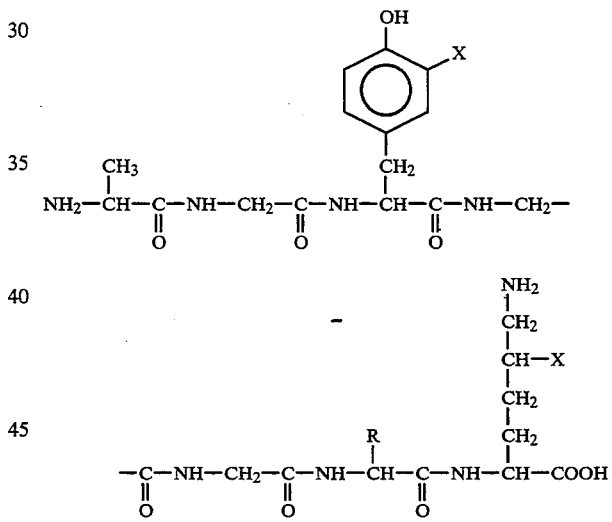

wherein each substituent X is independently a hydrogen atom or a hydroxyl group, and the substituent R is a methylethyl, 1-methylpropyl or 2-methylpropyl group, so that the penultimate group from the C-terminal of said peptide is a valine, isoleucine, or leucine.

2. A heptapeptide according to claim 1, wherein each substituent X is a hydroxyl group and the substituent R is a methylethyl group.

* * * * *